US006180369B1

(12) United States Patent
Vafai (10) Patent No.: US 6,180,369 B1
(45) Date of Patent: Jan. 30, 2001

(54) VARICELLA-ZOSTER VIRUS ANTIGEN

(75) Inventor: Abbas Vafai, Rockford, IL (US)

(73) Assignee: Research Corporation Technologies, Inc., Tucson, AZ (US)

(*) Notice: Under 35 U.S.C. 154(b), the term of this patent shall be extended for 0 days.

(21) Appl. No.: 08/469,191

(22) PCT Filed: Oct. 4, 1991

(86) PCT No.: PCT/US91/07280

§ 371 Date: Mar. 19, 1992

§ 102(e) Date: Mar. 19, 1992

(87) PCT Pub. No.: WO92/06989

PCT Pub. Date: Apr. 30, 1992

Related U.S. Application Data (62) Division of application No. 08/271,397, filed on Jul. 6, 1994, now Pat. No. 5,824,319, which is a continuation of application No. 07/864,961, filed as application No. PCT/US91/07280 on Oct. 4, 1991, now abandoned, which is a continuation-in-part of application No. 07/592,766, filed on Oct. 4, 1990, now abandoned.

(30) Foreign Application Priority Data

Oct. 4, 1991 (WO) .................................. PCT/US91/07280

(51) Int. Cl.[7] .......................... C07H 21/00; C07H 21/04; C12P 21/06; C12P 21/04
(52) U.S. Cl. .................... 435/69.3; 536/23.1; 536/23.72; 424/204.1; 424/230.1; 435/69.1; 435/70.1
(58) Field of Search .............................. 536/23.1, 23.72; 435/69.3, 69.1, 70.1; 424/204.1, 230.1

(56) References Cited

U.S. PATENT DOCUMENTS

| 4,008,317 | 2/1977 | Gits . |
|---|---|---|
| 4,016,043 | 4/1977 | Schuurs et al. . |
| 4,347,311 | 8/1982 | Schmitz . |
| 4,663,277 | 5/1987 | Wang . |
| 4,686,101 | 8/1987 | Ellis et al. . |
| 4,769,239 | 9/1988 | Ellis et al. . |
| 4,812,559 | 3/1989 | Ellis et al. . |
| 5,789,177 | * 8/1998 | Rijsewijk et al. . |
| 5,824,319 | * 10/1998 | Vafai . |

FOREIGN PATENT DOCUMENTS

| 0 192 902 | 9/1986 | (EP) . |
|---|---|---|
| 0 192 902 | * 9/1987 | (EP) . |
| 0405867A1 | 1/1991 | (EP) . |
| 0406857A1 | 1/1991 | (EP) . |
| 01252279 | 3/1988 | (JP) . |
| 3232897 | * 10/1991 | (JP) . |
| WO/85/04587 | 10/1985 | (WO) . |

OTHER PUBLICATIONS

Fletcher et al, Virology, 193: 762–773, 1993.*

Adams, et al. (1989) "Restriction Fragment Differences Between the Genomes of the Oka Varicella Vaccine Virus and American Wild–Type Varicella–Zoster Virus," *J. Med. Virol.* 29:38–45.

Cabirac, et al. (1988) "Expression of Varicella–Zoster Virus Glycoprotein I in Cells Infected with a Vaccinia Virus Recombinant," *Virus Research* 10:205–214.

Claesson–Welsh, et al. (1987) "Amino–Terminal Sequence, Synthesis and Membrane Insertion of Glycoprotein B of Herpes Simplex Virus Type 1," *J. Virol.* 61:1–7.

Davison, et al. (1986) "The Complete DNA Sequence of Varicella–Zoster Virus," *J. Gen. Virol.* 67:1759–1816.

Davison, et al. (1986) "New Common Nomenclature for Glycoprotein Genes of Varicella–Zoster Virus and Their Glycosylated Products," *J. Virol.* 57:1195–1197.

Diaz et al. (1988) "Immunity to Whole Varicella–Zoster Virus Antigen and Glycoproteins I and p170: Relation to the Immunizing Regimen of Live Attenuated Varicella Vaccine," *J. Infect. Dis.* 158:1245–1252.

Englund et al. (1989) "Placebo–Controlled Trial of Varicella Vaccine Given With or After Measles–Mumps–Rubella Vaccine," *J. Pediatr.* 114:37–44.

Hobman et al. (1988) "Translocation of Rubella Virus Glycoprotein E1 into the Endoplasmic Reticulum," *J. Virol.* 62:4259–4264.

Hope et al. (1985) "GCN4 Protein, Synthesized In Vitro, Binds HIS3 Regulatory Sequences: Implications for General Control of Amino Acid Biosynthetic Genes in Yeast," *Cell* 43:177–186.

Kato et al. (1989) "Transcription Mapping of Glycoprotein I (gpI) and gpIV of Varicella–Zoster Virus and Immunological Analysis of the gpI Produced in Cells Infected with the Recombinant Vaccinia Virus," *Microbiol. Immunol.* 33:299–312.

(List continued on next page.)

*Primary Examiner*—Nita Minnfield
(74) *Attorney, Agent, or Firm*—Scully, Scott, Murphy & Presser (57) ABSTRACT

The present invention relates to the construction of a recombinant plasmid which is capable of expressing a secretory truncated glycoprotein (Tgp) of Varicella-zoster virus (VZV) in mammalian cells. The secretory Tgp of the present invention contains at least one epitope capable of inducing antibody response. The present invention contemplates the production and utilization of this secretory Tgp in a vaccine against chickenpox and/or shingles. The present invention is also directed towards the use of the secretory Tgp in diagnostic assays for detection of VZV. The present invention is also directed to first antibodies specific to secretory Tgp and to second antibodies specific to the first antibodies. These second antibodies are also useful in diagnostic assays for VZV.

15 Claims, 6 Drawing Sheets

OTHER PUBLICATIONS

Litwin et al. (1990) "Cell Surface Expression of the Varicella–Zoster Virus Glycoproteins and Fc Receptor," *Virology* 178:263–272.

Makikado et al. (1990) "Recombinant Preparation of Glycoprotein gpII of Varicella–Zoster Virus (VZV) in Eukaryotes and Its Use," *Chemical Abstracts* 112:497, Abstract No. 215209s.

Straus et al. (1988) "Varicella–Zoster Virus Infections," *Ann. Intern. Med.* 108:221–237.

Vafai et al. (1984) "Analysis of Three Late Varicella–Zoster Virus Proteins, A 125,000–Molecular–Weight Protein and gp1 and gp3," *J. Virol.* 52:953–959.

Vafai et al. (1987) "Induction of Antibody Against In Vitro Translation Products Encoded by Varicella–Zoster Virus Glycoprotein Genes," *Virus Research* 7:325–333.

Vafai et al. (1988) "Recognition of Similar Epitopes on Varicella–Zoster Virus gpI and gpIV by Monoclonal Antibodies," *J. Virol.* 62:2544–2551.

Vafai et al. (1989) "Existence of Similar Antigenic–Sites on Varicella–Zoster Virus gpI and gpIV," *Virus Research* 13:319–336.

* cited by examiner

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 159 amino acids
      (B) TYPE: amino acid
      (C) STRANDEDNESS: single
      (D) TOPOLOGY: linear    (ii) MOLECULE TYPE: peptide    (ix) FEATURE:
      (A) NAME/KEY: Peptide
      (B) LOCATION: 160..661

(xi) SEQUENCE DESCRIPTION: SEQ ID NO:1:

```
Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Thr Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
                100                 105                 110

Arg Leu Met Gln Pro Thr Gln Met Ser Ala Gln Glu Asp Leu Gly Asp
            115                 120                 125

Asp Thr Gly Ile His Val Ile Pro Thr Leu Asn Gly Asp Asp Arg His
        130                 135                 140

Lys Ile Val Asn Val Asp Gln Arg Gln Tyr Gly Asp Val Phe Lys
145                 150                 155
```

(2) INFORMATION FOR SEQ ID NO:2:

(i) SEQUENCE CHARACTERISTICS:
      (A) LENGTH: 511 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

```
Met Gly Thr Val Asn Lys Pro Val Val Gly Val Leu Met Gly Phe Gly
1               5                  10                  15

Ile Ile Thr Gly Thr Leu Arg Ile Thr Asn Pro Val Arg Ala Ser Val
            20                  25                  30

Leu Arg Tyr Asp Asp Phe His Thr Asp Glu Asp Lys Leu Asp Thr Asn
            35                  40                  45

Ser Val Tyr Glu Pro Tyr Tyr His Ser Asp His Ala Glu Ser Ser Trp
50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
            115                 120                 125

Asp Thr Gly Ile His Val Ile Pro Thr Leu Asn Gly Asp Asp Arg His
130                 135                 140

Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
            195                 200                 205

Thr Gly Asp Ala Ala Pro Ala Ile Gln His Ile Cys Leu Lys His Thr
210                 215                 220

Thr Cys Phe Gln Asp Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
            275                 280                 285

Leu Arg Thr Glu Lys Gln Tyr Leu Gly Val Tyr Ile Trp Asn Met Arg
            290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
            355                 360                 365

Glu Ala Pro Phe Asp Leu Leu Leu Glu Trp Leu Tyr Val Pro Ile Asp
            370                 375                 380

Pro Thr Cys Gln Pro Met Arg Leu Tyr Ser Thr Cys Leu Tyr His Pro
385                 390                 395                 400
```

-continued

```
Asn Ala Pro Gln Cys Leu Ser His Met Asn Ser Gly Cys Thr Phe Thr
            405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
            435                 440                 445

Glu Pro Ser Phe Gly Leu Ile Leu His Asp Gly Gly Thr Thr Leu Lys
        450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
            485                 490                 495

Val Asp His Phe Val Asn Ala Ile Glu Glu Arg Gly Phe Pro Pro
            500                 505                 510
```

VARICELLA-ZOSTER VIRUS ANTIGEN

This is a divisional of application Ser. No. 08/271,397, filed on Jul. 6, 1994, now U.S. Pat. No. 5,824,319, which is a continuation application of U.S. Ser. No. 07/864,961 filed on May 12, 1992, now abandoned, which is a 371 of PCT/US91/07280 filed on Oct. 4, 1991 which is a continuation-in-part of U.S. Ser. No. 07/592,766 filed on Oct. 4, 1990, now abandoned.

This invention was made with Government support under Grant No. P01-AG-07347-01 awarded by the National Institutes of Health. The Government has certain rights in the invention.

The present invention relates to the construction of a recombinant plasmid which is capable of expressing a secretory truncated glycoprotein (Tgp) of Varicella-zoster virus (VZV) in mammalian cells. The secretory Tgp of the present invention contains at least one epitope capable of inducing antibody response. The present invention contemplates the production and utilization of this secretory Tgp in a vaccine against chickenpox and/or shingles. The present invention is also directed towards the use of the secretory Tgp in diagnostic assays for detection of VZV. The present invention is also directed to first antibodies specific to secretory Tgp and to second antibodies specific to the first antibodies. These second antibodies are also useful in diagnostic assays for VZV.

Varicella-zoster virus is the causative agent of childhood chickenpox (varicella) and shingles (zoster), two distinct clinical manifestations. Varicella is the outcome of the primary encounter (infection) with VZV, whereas zoster is the result of VZV reactivation which occurs predominantly in aging and immunosuppressed individuals, including cancer and AIDS patients. There are 2.5 million estimated cases of chickenpox and 1.2 million cases of shingles per year in the United States. It is expected that the number of shingles patients will increase as the population ages. One of the most common complications of shingles includes postherpetic neuralgia which is characterized by interactable pain lasting for four weeks to several years after the onset of skin rash. Other complications of VZV reactivation (shingles) include encephalitis, pneumonitis and disseminated zoster.

VZV is a member of the alpha herpesvirus family. VZV contains a linear double-stranded DNA genome of approximately 125,000 base pairs and consists of the sequence of a long unique (U1)-inverted short repeat (IRs)-short unique (Us)-terminal short repeat (TRs). VZV DNA encodes five glycoproteins, designated gpI, gpII, gpIII, gpIV and gpV, of which gpI through gpIV are readily detected in infected cells and in VZ virions (Davison and Scott, *J. Gen. Virol.*, 67:1759–1816, 1986; Davison, et al., *J. Virol.* 57:1195–1197, 1986). These glycoproteins are highly immunogenic and elicit both neutralizing antibodies and cell-mediated immune response in the infected individuals (Davison, et al., supra, 1986).

VZV gpI, which is the most abundant and immunogenic of the virion envelope glycoproteins, elicits the formation of complement-dependent neutralizing antibodies and also mediates antibody-dependent cellular cytotoxicity. The gene encoding gpI is located in the unique short (Us) region of the VZV genome. One of the major antibody-binding sites (epitope) on a VZV glycoprotein has been identified in VZV gpI (Vafai, et al., *J. Virol.* 62:2544 (1988)). The synthetic peptides (14 amino acid residues) comprising this epitope (designated e1) induced antibody response which was recognized by a high-mannose intermediate (82 kDa) but not the mature form (95 kDa) of VZV gpI (Vafai, et al., *Virus Res.* 13:319–336, 1989). These results along with the lack of VZV neutralizing activity of anti-peptide antibodies suggested that the state and extent of O-linked and/or N-linked glycosylation of e1 epitope affect the conformation of gpI or result in steric hindrances which influence the antigenic determinant recognized by anti-peptide antibodies.

An attenuated varicella-zoster virus vaccine has been used in Japan against chickenpox infection in leukemic children as well as for routine vaccination in early childhood. This vaccine is currently being tested in the United States in children with leukemia and is expected to be used in healthy children and for the prevention of VZV reactivation (shingles) in the elderly population. Although the attenuated varicella vaccine has been shown to be safe and effective in inducing immunity against VZV infection, however, similar to natural infection, attenuated varicella vaccine becomes latent in human dorsal root ganglia and may reactivate to produce shingles with its attendant neurologic complications of postherpetic neuralgia and encephalitis.

Therefore, a subunit vaccine which would avoid and eliminate latency is desirable for immunization of children as well as for boosting immune response in the elderly who are more susceptible to VZV reactivation (shingles). Such subunit vaccine as contemplated by the present invention may be prepared by construction of recombinant viruses (e.g., vaccinia virus) expressing one or more VZV glycoproteins or, as particularly contemplated by the present invention, may be composed of secretory highly immunogenic VZV glycoprotein(s) which can be prepared and purified in large quantities and used for immunization and/or boosting the immune response against VZV infection. In addition, such highly purified VZV glycoproteins can be used as a diagnostic tool for the assessment of the immune status to VZV infection in immunosuppressed individuals (leukemic children, AIDS and cancer patients) as well as in vaccinated individuals and the elderly population.

The gene for VZV gpI has been previously isolated, inserted into a plasmid and incorporated into a vaccinia virus expression system. Although gpI protein was produced by the vaccinia expression system, the product remained within the cells and was therefore unsuitable for eliciting an antigenic response in vivo.

The innovation of the present invention resides in the construction of an expression vector which produces a truncated form of VZV gp which is secreted from mammalian cells.

The applications of the present recombinant vaccinia viruses expressing secretory truncated VZV glycoproteins containing one or more highly immunogenic viral epitopes include: (1) using such recombinant viruses as subunit vaccines against VZV infection, wherein secretion of VZV glycoproteins following vaccination provides a stronger immune response to VZV glycoproteins as well as to VZV infection; (2) using large quantities of highly purified and immunogenic secretory VZV glycoproteins containing one or more epitopes as a subunit vaccine against primary VZV infection (chickenpox) in healthy children as well as in immunocompromised individuals and for boosting immunity against VZV reactivation (shingles) in the elderly; and (3) using purified preparations of secretory truncated VZV glycoproteins in diagnostic kits as highly specific target antigens for the detection and assessment of antibody status to VZV glycoproteins. Since VZV reactivation is common in cancer and AIDS patients, there is also a need for the serological diagnosis of VZV infection in these patients. In addition, since VZV reactivation in the growing population of elderly individuals results in pain prior to the onset of clinical symptoms and may also result in encephalitis, pneumonitis and disseminated zoster, the only hope for an early treatment of these patients lies in a rapid means of diagnosis. Application of the present recombinantly prepared secretory VZV glycoproteins in diagnostic kits can provide a rapid and inexpensive means for diagnosis of VZV infection.

The present invention is directed to an expression vector for secretory truncated VZV gp and construction of said vector which permits extracellular secretion of the VZV protein.

More specifically, the present invention is directed to a recombinant DNA expression vector comprising a nucleotide sequence capable of expressing in an infected, transfected or transformed host a Varicella-zoster virus (VZV) truncated glycoprotein (gp) which is secreted extracellularly from said host and wherein said glycoprotein causes a VZV antibody response in mammals.

Another aspect of this invention contemplates the recombinant production of secretory truncated VZV gpI, II, III, IV or V in mammalian cells.

A further aspect of the present invention is directed to a process for producing secretory truncated Varicella-zoster virus gp.

More specifically, the present invention is directed to a process for producing a secretory truncated Varicella-zoster virus glycoprotein, said process comprising the steps of:

a) providing a vector comprising a nucleotide sequence coding for said polypeptide, wherein the nucleotide sequence is capable of being expressed by a host containing the vector, and wherein the nucleotide sequence is selected from the group of nucleic acids capable of encoding with a continuous nucleotide sequence a Varicella-zoster virus glycoprotein having a substantial portion of the region coding for the C-terminal region of the glycoprotein deleted whereby said gp is secreted extracellularly from said host and wherein said gp is capable of causing a VZV antibody response in mammals;

b) incorporating the vector into the host; and c) maintaining the host containing the vector under conditions suitable for expression of the nucleotide sequence into said glycoprotein.

Yet another aspect of the present invention relates to the secretory truncated VZV gp.

A further aspect of this invention is directed to using the secretory truncated VZV gp in diagnostic assays for VZV.

Still another aspect of the present invention is the use of the secretory truncated VZV gp to produce a vaccine to chickenpox and/or shingles.

Yet another aspect of this invention contemplates a kit for diagnosing and monitoring of VZV antibody.

More specifically, the present invention contemplates a compartmentalized kit for detection of secretory truncated VZV gp antibody, comprising at least one first container adapted to contain an antibody having specificity for said VZV gp antibody, and at least one second container adapted to contain a reporter molecule capable of detecting the antibody of said first container.

FIG. 2 demonstrates expression of a truncated VZV gpI by recombinant vaccinia virus. BSC-1 cells were infected with recombinant vaccinia virus carrying a truncated VZV gpI as described in FIG. 2 (designated VVTgpIBglII) and containing e1 epitope. After 22 hours, infected cells were labeled with [35S] methionine for 1 hour and cell lysates were prepared as described in the Examples. Cell lysates were immunoprecipitated with the following monoclonal antibodies (MAbs) and a human serum and analyzed by SDS-12% polyacrylamide PAGE:MAb79.7, directed against e1 epitope; human serum (H-serum) from a VZV seropositive individual; MAbC1, directed against VZV gpI and recognizing epitope(s) other than e1; MAbG7, directed against VZV gpI and recognizing only the glycosylated form of e1 epitope; MAbG6, directed against VZV gpIV; MAbF8, directed against VZV gpII; and MAbE10, directed against VZV gpIII. The size (in kilodaltons) of precursor and glycosylated form of the TgpIBglII are shown on the left.

FIG. 3 demonstrates the expression and secretion of TgpIXmaIII from the infected cells. In the left panel, cells were infected with VVTgpIXmaIII and after 22 hours, infected cells were pulse-labeled with [$^{35}$S]methionine (200 µCi/ml) for 1 hour. Cells were harvested, cell lysates (CL) were prepared, immunoprecipitated with MAbs and analyzed by 9% SDS-PAGE. In the right panel, cells were infected and labeled as described above. Following the pulse-labeling period, cells were washed five times with serum-free media and incubated in serum-free media at 37° for 2 hours. Tissue culture fluids (TCF) were harvested, immunoprecipitated with MAbs and analyzed by 9% SDS-PAGE. MAbF9 is directed against the VZV nucleocapsid protein. The sizes (in kilodaltons) of the core and processed forms of TgpIXmaIII are indicated on the left.

FIG. 4 demonstrates expression and secretion of TgpIBglII from the infected cells. In the left panel, cells were infected with VVTgpIBglII and after 22 hours, infected cells were pulse-labeled with [35S] methionine (300 µci/ml) for 10 min. Cells were either harvested or washed with serum-free medium and the label was chased for 1, 2, 3 and 7 hours. Uninfected cells (Un) were pulse-labeled for 10 min. and chased for 7 hours. Cell lysates (CL) were prepared and immunoprecipitated with MAb79.7 (a) which is directed against VZV gpI e1 epitope and MAbC1 (b) which is directed against VZV gpI but only recognizes epitope(s) other than e1. Right panel, tissue culture fluid (TCF) from uninfected (Un) and VVTgpIBglII-infected cell chased for 1, 2, 3 and 7 hours, were immunoprecipitated with MAb79.7 (a) and MAbC1(b). Samples were analyzed by SDS-12% polyacrylamide PAGE as described in materials and methods. Apparent sizes (in kilodaltons) of precursor and glycosylated mature forms of TgpI are shown.

FIG. 5 demonstrates expression of recombinant vaccinia virus carrying a full-size VZV gpI gene (designated VVgpI). Cells were infected with VVgpI (Cabirac, et al., 1988) and after 22 hours, cells were pulse-chased as described in FIG. 3 and cell lysates (CL) and tissue culture fluids (TCF) from uninfected (Un) and VVgpI-infected cells (VVgpI) were immunoprecipitated with MAb79.7 which is directed against VZV gpI e1 epitope. Samples were analyzed by SDS-8% polyacrylamide PAGE as described in the Examples. The size-range of precursor-products of VZV gpI (Vafai, et al., 1988) is indicated.

methionine (300 μci/ml) for 10 min. in the absence or presence of (15 μg/ml) tunicamycin (TM), which inhibits the addition of N-linked oligosaccharides to native VZV gpI. Cells were either harvested or washed and chased for 2 hours in the absence or presence of TM (15 μg/ml). Cell lysates were prepared and immunoprecipitated with MAbC1 (a) which recognizes both VZV gpI and gpIV and rabbit anti-VVTgpI antibodies (RAnti-VVTgpI). Samples were analyzed by SDS-8% polyacrylamide PAGE as described in the Examples. Apparent sizes (in kilodaltons) of precursor-products of VZV gpI and gpIV (Vafai, et al., supra, 1988) are indicated on the right. Lysozyme (14.3 kDa), β-lactoglobulin (18.4 kDa), α-chymotrypsinogen (25.7 kDa), ovalbumin (43.0 kDa), bovine serum albumin (68.0 kDa), phosphorylase B (97.4 kDa), and myosin (200.0 kDa) were used as internal size markers.

DETAILED DESCRIPTION OF THE INVENTION

The present invention contemplates the construction of a recombinant plasmid having a truncated VZV gp (I, II, III, IV or V) gene carrying at least one epitope capable of inducing antibody response in mammalian cells. In particular, the present invention relates to a vaccinia virus expression system capable of producing truncated VZV gp which can be secreted from mammalian cells into a host organism in vivo.

In one embodiment, the present invention contemplates the construction of a recombinant plasmid having a secretory truncated VZV gpI (referred to as TgpIBglII or VVTgpIBglII) carrying e1 epitope and production of said protein by the vaccinia virus expression vector in mammalian cells as described herein.

In another embodiment, the present invention contemplates the construction of a recombinant plasmid having a secretory truncated VZVgpI (referred to as TgpIXmaIII or VVTgpIXmaIII) and production of said protein by the vaccinia virus expression vector in mammalian cells as described herein.

In another embodiment, this invention contemplates the preparation and use of a vaccine composition for the treatment of chickenpox and/or shingles.

Previously used vaccines have generally comprised (I) an attenuated live virus type of vaccine in which the virus has been rendered avirulent but not killed by some form of genetic attenuation; or (II) specific viral components isolated and purified from the virus and inactivated by formalin or some other chemical or physical treatment. The present invention contemplates Type II vaccines, wherein the specific viral components isolated and purified from the virus and inactivated by formalin or other treatments are contemplated to be secretory truncated VZV gp. Unless otherwise specified in the Specification and Claims, VZV gp means VZV gpI, gpII, gpIII, gpIV or gpV. Furthermore, "truncated" as used in the Specification and Claims is defined as a segment of indeterminate size of the VZV gp (but not the full-sized VZV gp) wherein a substantial portion (or all) of the amino acid sequence C-terminal of the region has been deleted. The present invention also contemplates the preparation of recombinant secretory truncated VZV gp for use in a vaccine against VZV.

In another embodiment, the present invention is directed to a Type II vaccine which contains secretory truncated VZV gp.

By vaccine is meant an agent used to stimulate the immune system of a living organism so that immunological protection against future harm caused by an infectious agent is provided. Administration of a vaccine contemplated by the present invention to the patient (or animal) may be by any known or standard techniques. These include oral ingestion, intestinal intubation, or broncho-nasal spraying. Other methods of administration, such as intravenous injection, that allow the carrier microbe to reach the human or animal's bloodstream may be acceptable when the carrier microbe is unable to reproduce.

In a further embodiment, the present invention contemplates a diagnostic assay for VZV, and additionally, a diagnostic kit for the detection of VZV antibody in various clinical manifestations of VZV infection and in vaccinated individuals.

Figure 1:
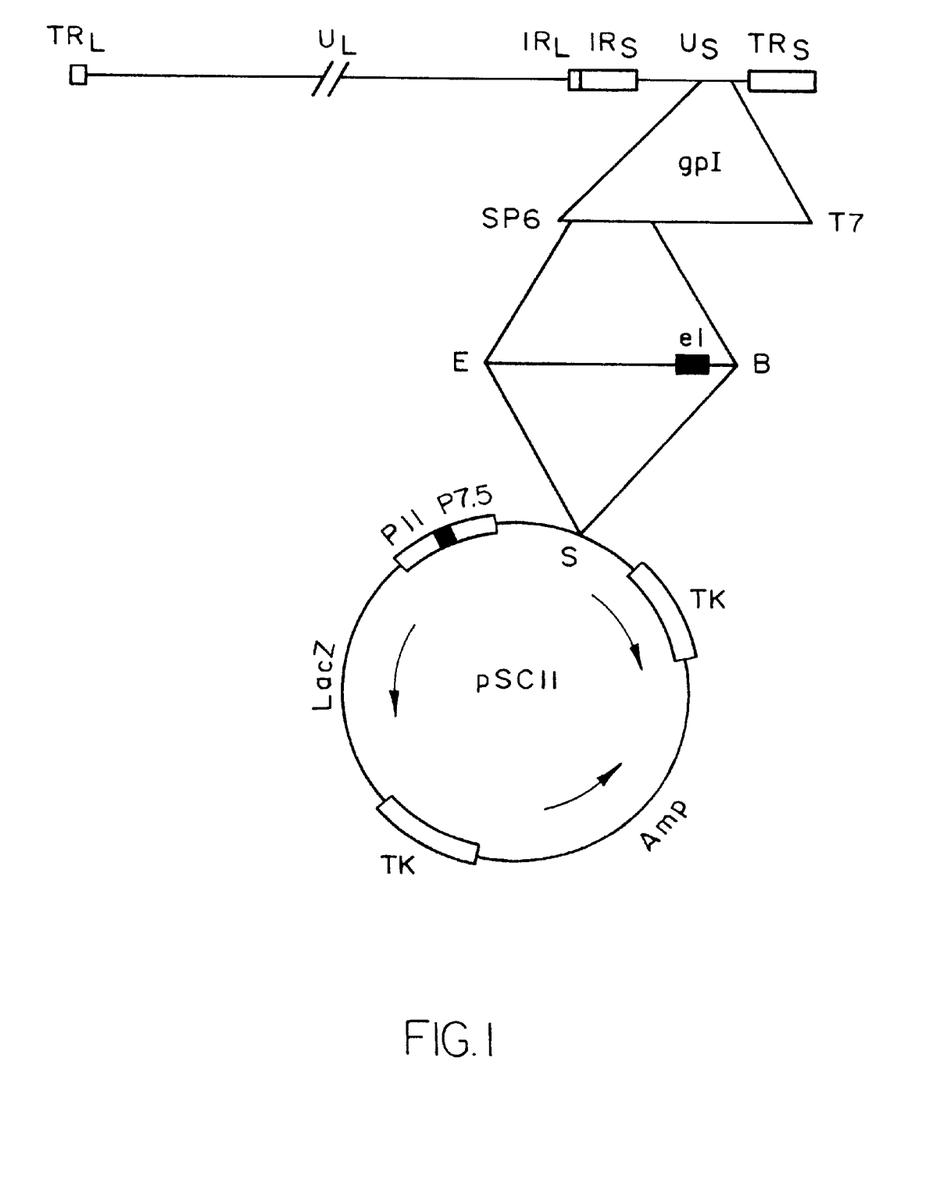
FIG. 1 is a schematic representation of the construction of a recombinant plasmid carrying a truncated VZV gpI gene having the e1 epitope. VZV gpI gene cloned in pGEM-4 transcription vector (Vafai, et al., supra, 1988) was cleaved with BglII (B) restriction enzyme downstream from e1 epitope and with EcoRI (E) in the pGEM polylinker. The truncated gpI gene was electroeluted, blunt-ended and cloned at the SmaI (S) of vaccinia virus insertion vector pSC11 as described in detail in the Examples.

The present invention represents a step forward from earlier attempts to obtain VZV gp protein. Previously, the known gene for VZV gpI was inserted into a plasmid and incorporated into a vaccinia virus expression system. However, the VZV gpI produced by this expression system remained intracellular, i.e., within the mammalian cells, thus failing to permit antigenic activity (the production of antibodies). The discovery of the present invention is an expression vector in vaccinia virus capable of producing, i.e., expressing a truncated VZV gp such as, for example, gpI, gpII, gpIII, gpIV or gpV, which is secreted from mammalian cells. This truncated gp further contains an epitope which causes the production of neutralizing antibodies in invaded hosts. The VZV gp gene is cloned in pGEM transcription vector, cleaved with restriction enzymes such as, for example, EcoRI and Bgl II restriction enzymes (to remove part or substantially all of the C-terminal region), blunt-ended and cloned at the SmaI site of vaccinia virus insertion vector pSC11 as shown in FIG. 1.

In a preferred embodiment, the present invention contemplates the construction of a recombinant DNA expression vector as follows. A 592-bp DNA fragment containing 17 bp from pGEM-4 polylinker upstream from SmaI site and 575 nucleotides (spanning nucleotides 115712 to 116287 of the VZV genome) is cleaved with EcoRI and BglII, respectively, from pGEM recombinant carrying a blunt-ended VZV BglI DNA fragment (spanning nucleotides 115712 to 118181) containing gpI open reading frame (Davison and Scott, supra, p. 1800–1801, 1986, incorporated herein by reference). The truncated gpI (TgpI) DNA, encoding the N-terminal region of gpI with 159 amino acid residues and an estimated size of 17.5 kDa, is blunt-ended and cloned at the SmaI site of pSC11 plasmid vector (FIG. 1) and inserted into vaccinia genome as described in the Examples. The truncated gpI (TgpIBglII) contains e1 epitope located within 14 amino acid residues between residues 109 to 123 of the predicted amino acid sequences of VZV gpI (Vafai, et al., supra, 1988; Vafai, et al., supra, 1989). The TgpIBglII lacks the 464 amino acid residues at the C-terminal region of gpI, which apparently includes the membrane-anchoring region of gpI.

In another preferred embodiment, the present invention contemplates the construction of a recombinant expression vector as follows. A 1647-bp DNA fragment containing 17 bp from pGEM-4 polylinker upstream from the SmaI site and 1630 VZV nucleotides (spanning nucleotides 115712 to 117342 of the VZV genome) is cleaved with EcoR1 and XmaIII, respectively, from pGEM recombinant carrying a blunt-ended VZV BglI DNA fragment (spanning nucleotides 115712 to 118181) and containing gpI open reading frame (Davison and Scott, supra, p. 1800–1801, 1986). The truncated gpI (TgpIXmaIII) DNA, encoding the N-terminal region of gpI with 511 amino acid residues, was blunt-ended and cloned at the SmaI site of pSC11 plasmid vector and inserted into the vaccinia virus genome as described in the Examples. The TgpIXmaIII lacks the 112 amino acid residues at the C-terminal region of gpI, which apparently includes the membrane-anchoring region of gpI.

The present invention is directed to a recombinant DNA expression vector as described above which includes a nucleotide sequence capable of expressing in an infected, transfected or transformed host a Tgp which is secreted extracellularly from said host and which is capable of causing an antibody response in mammals, and preferably a mature polypeptide defined by the 159 amino acid sequence (Seq. Id. No. 1):

| | | | | | | | | | | | | | |
|---|---|---|---|---|---|---|---|---|---|---|---|---|---|
| Met | Gly | Thr | Val | Asn | Lys | Pro | Val | Val | Gly | Val | Leu | Met | Gly | Phe | 15 |
| Gly | Ile | Ile | Thr | Gly | Thr | Leu | Arg | Ile | Thr | Asn | Pro | Val | Arg | Ala | 30 |
| Ser | Val | Leu | Arg | Tyr | Asp | Asp | Phe | His | Thr | Asp | Glu | Asp | Lys | Leu | 45 |
| Asp | Thr | Asn | Ser | Val | Tyr | Glu | Pro | Tyr | Tyr | His | Ser | Asp | His | Ala | 60 |
| Glu | Ser | Ser | Trp | Val | Asn | Arg | Gly | Glu | Ser | Ser | Arg | Lys | Ala | Tyr | 75 |
| Asp | His | Asn | Ser | Pro | Tyr | Ile | Trp | Pro | Arg | Asn | Asp | Tyr | Asp | Gly | 90 |
| Phe | Leu | Glu | Asn | Ala | His | Glu | His | His | Gly | Val | Tyr | Asn | Gln | Gly | 105 |
| Arg | Gly | Ile | Asp | Ser | Gly | Glu | Arg | Leu | Met | Gln | Pro | Thr | Gln | Met | 120 |
| Ser | Ala | Gln | Glu | Asp | Leu | Gly | Asp | Asp | Thr | Gly | Ile | His | Val | Ile | 135 |
| Pro | Thr | Leu | Asn | Gly | Asp | Asp | Arg | His | Lys | Ile | Val | Asn | Val | Asp | 150 |
| Gln | Arg | Gln | Tyr | Gly | Asp | Val | Phe | Lys | | | | | | | 159 | or a mature polypeptide defined by the 511 amino acid sequence (Seq. Id. No. 2):

| | | | | | | | | | | | | | |
|---|---|---|---|---|---|---|---|---|---|---|---|---|---|
| Met | Gly | Thr | Val | Asn | Lys | Pro | Val | Val | Gly | Val | Leu | Met | Gly | Phe | 15 |
| Gly | Ile | Ile | Thr | Gly | Thr | Leu | Arg | Ile | Thr | Asn | Pro | Val | Arg | Ala | 30 |
| Ser | Val | Leu | Arg | Tyr | Asp | Asp | Phe | His | Thr | Asp | Glu | Asp | Lys | Leu | 45 |
| Asp | Thr | Asn | Ser | Val | Tyr | Glu | Pro | Tyr | Tyr | His | Ser | Asp | His | Ala | 60 |
| Glu | Ser | Ser | Trp | Val | Asn | Arg | Gly | Glu | Ser | Ser | Arg | Lys | Ala | Tyr | 75 |
| Asp | His | Asn | Ser | Pro | Tyr | Ile | Trp | Pro | Arg | Asn | Asp | Tyr | Asp | Gly | 90 |
| Phe | Leu | Glu | Asn | Ala | His | Glu | His | His | Gly | Val | Tyr | Asn | Gln | Gly | 105 |
| Arg | Gly | Ile | Asp | Ser | Gly | Glu | Arg | Leu | Met | Gln | Pro | Thr | Gln | Met | 120 |
| Ser | Ala | Gln | Glu | Asp | Leu | Gly | Asp | Asp | Thr | Gly | Ile | His | Val | Ile | 135 |
| Pro | Thr | Leu | Asn | Gly | Asp | Asp | Arg | His | Lys | Ile | Val | Asn | Val | Asp | 150 |
| Gln | Arg | Gln | Tyr | Gly | Asp | Val | Phe | Lys | Gly | Asp | Leu | Asn | Pro | Lys | 165 |
| Pro | Gln | Gly | Gln | Arg | Leu | Ile | Glu | Val | Ser | Val | Glu | Glu | Asn | His | 180 |
| Pro | Phe | Thr | Leu | Arg | Ala | Pro | Ile | Gln | Arg | Ile | Tyr | Gly | Val | Arg | 195 |
| Tyr | Thr | Glu | Thr | Trp | Ser | Phe | Leu | Pro | Ser | Leu | Thr | Cys | Thr | Gly | 210 |
| Asp | Ala | Ala | Pro | Ala | Ile | Gln | His | Ile | Cys | Leu | Lys | His | Thr | Thr | 225 |
| Cys | Phe | Gln | Asp | Val | Val | Val | Asp | Val | Asp | Cys | Ala | Glu | Asn | Thr | 240 |
| Lys | Glu | Asp | Gln | Leu | Ala | Glu | Ile | Ser | Tyr | Arg | Phe | Gln | Gly | Lys | 255 |
| Lys | Glu | Ala | Asp | Gln | Pro | Trp | Ile | Val | Val | Asn | Thr | Ser | Thr | Leu | 270 |
| Phe | Asp | Glu | Leu | Glu | Leu | Asp | Pro | Pro | Glu | Ile | Glu | Pro | Gly | Val | 285 |
| Leu | Lys | Val | Leu | Arg | Thr | Glu | Lys | Gln | Tyr | Leu | Gly | Val | Tyr | Ile | 300 |
| Trp | Asn | Met | Arg | Gly | Ser | Asp | Gly | Thr | Ser | Thr | Tyr | Ala | Thr | Phe | 315 |

-continued

| | | | | | | | | | | | | |
|---|---|---|---|---|---|---|---|---|---|---|---|---|
| Leu | Val | Thr | Trp | Lys | Gly | Asp | Glu | Lys | Thr | Arg | Asn | Pro | Thr | Pro | 330 |
| Ala | Val | Thr | Pro | Gln | Pro | Arg | Gly | Ala | Glu | Phe | His | Met | Trp | Asn | 345 |
| Tyr | His | Ser | His | Val | Phe | Ser | Val | Gly | Asp | Thr | Phe | Ser | Leu | Ala | 360 |
| Met | His | Leu | Gln | Tyr | Lys | Ile | His | Glu | Ala | Pro | Phe | Asp | Leu | Leu | 375 |
| Leu | Glu | Trp | Leu | Tyr | Val | Pro | Ile | Asp | Pro | Thr | Cys | Gln | Pro | Met | 390 |
| Arg | Leu | Tyr | Ser | Thr | Cys | Leu | Tyr | His | Pro | Asn | Ala | Pro | Gln | Cys | 405 |
| Leu | Ser | His | Met | Asn | Ser | Gly | Cys | Thr | Phe | Thr | Ser | Pro | His | Leu | 420 |
| Ala | Gln | Arg | Val | Ala | Ser | Thr | Val | Tyr | Gln | Asn | Cys | Glu | His | Ala | 435 |
| Asp | Asn | Tyr | Thr | Ala | Tyr | Cys | Leu | Gly | Ile | Ser | His | Met | Glu | Pro | 450 |
| Ser | Phe | Gly | Leu | Ile | Leu | His | Asp | Gly | Gly | Thr | Thr | Leu | Lys | Phe | 465 |
| Val | Asp | Thr | Pro | Glu | Ser | Leu | Ser | Gly | Leu | Tyr | Val | Phe | Val | Val | 480 |
| Tyr | Phe | Asn | Gly | His | Val | Glu | Ala | Val | Ala | Tyr | Thr | Val | Val | Ser | 495 |
| Thr | Val | Asp | His | Phe | Val | Asn | Ala | Ile | Glu | Glu | Arg | Gly | Phe | Pro | 510 |
| Pro | | | | | | | | | | | | | | | 511 |

The infected, transfected or transformed host contemplated by the present invention can be mammalian cells such as, for example, green monkey kidney cells (BSC-1), COS monkey cells, HeLa cells, hamster kidney cells and human fibroblast cells. In addition, any human tissue is contemplated as a suitable host. The present invention contemplates that the infected, transformed or transfected cell as described above can be caused to produce and secrete Tgp (truncated VZV glycoprotein) and preferably, TgpIBglII as defined by Seq. Id. No. 1 or TgpIXmaIII by the recombinant DNA expression vector of the present invention.

The present invention also contemplates other secretory TgpIs. Other TgpIs containing other immunogenic epitopes can be generated by cloning and expressing various truncated gpI genes. The other gpIs can be obtained, for example, by utilizing the following restriction enzymes:

a) EcoPI and EcoRI, wherein EcoPI cleaves at nucleotide 115751 and results in generation of a 276 amino acid sequence;

b) BstE2 and EcoRI, wherein BstE2 cleaves at nucleotide 116754 and results in generation of a 316 amino acid sequence;

c) Nde1 and EcoRI, wherein Nde1 cleaves at nucleotide 116831 and results in generation of a 341 amino acid sequence; and d) EcoRI and EcoRI wherein EcoRI cleaves at nucleotide 117034 and results in generation of a 408 amino acid sequence.

The various types of TgpI contemplated by the present invention as described above are specifically constructed to eliminate that portion of the C-terminal region of the nucleotide sequence encoding the region of VZV gp which prevents the extracellular expression of that VZV gp (such as gpI, gpII, gpIII, gpIV or gpV), i.e., apparently by eliminating the membrane anchoring region of the encoded protein. In preparing suitable expression vectors for such truncated secretory proteins, it is also necessary to maintain at least one epitope, e.g., e1, so that the encoded Tgp (extracellularly secreted) elicits an antibody response in the host. Provided with the discovery of the present invention one skilled in the art is able to construct various suitable expression vectors for use as vaccines and detection systems, all contemplated by the present invention.

The present invention also contemplates the modification of the recombinant DNA expression vector described above in order to obtain other truncated VZV gps (e.g., II, III, IV or V). The DNA sequence for VZV gpII is disclosed, for example, in Davison and Scott, *J. Gen. Virol.*, 67:1759–1816, 1986 at p. 1780–1781. The DNA sequence for VZV gpIII is in Davison and Scott, 1986 at p. 1784. The DNA sequence for VZV gpIV is in Davison and Scott, 1986 at p. 1800. The DNA sequence for VZV gpV is in Davison and Scott, 1986 at p. 1768–1769. In accordance with the teachings of the present invention, an artisan of ordinary skill in the art can then construct an expression which would contain the appropriate truncated VZV gpII, gpIII, gpIV or gpV gene capable of expressing secretory TgpII, TgpIII, TgpIV or TgpV.

The discovery of the present invention is directed to deleting the native (naturally occurring) VZV DNA encoding the C-terminal region of gpII, gpIII, gpIV or gpV, as described above for gpI, resulting in the production of TgpII, TgpIII, TgpIV or TgpV, which can be secreted outside of mammalian cells and resulting in antigenic activity, in vivo, i.e., stimulating antibody formation.

The present invention also contemplates a process for producing a secretory truncated Varicella-zoster virus gp. This process consists of the following steps:

a) providing a vector comprising a nucleotide sequence coding for said polypeptide, wherein the nucleotide sequence is capable of being expressed by a host containing the vector, and wherein the nucleotide sequence is selected from the group of nucleic acids capable of encoding with a continuous nucleotide sequence a Varicella-zoster virus gp wherein a substantial portion of VZV gp genome coding for the C-terminal region of the gp is deleted and wherein said gp is secreted extracellularly from said host and includes at least one epitope effecting an antibody response in a mammalian host, and such as, for example, a polypeptide of the open reading frame defined by the 159 amino acid sequence of Seq. Id. No. 1 or a polypeptide of the open reading frame defined by the 159 amino acid sequence of Seq. Id. No. 2;

b) incorporating the vector into the host; and c) maintaining the host containing the vector under conditions suitable for expression of the nucleotide sequence into said polypeptide. This process can include a promoter operationally associated with said nucleotide sequence. This process further contemplates said nucleotide sequence including a region of nucleotides capable of encoding a leader sequence.

The expression of recombinant vaccinia virus carrying the Tgp (VVTgp) can be analyzed by infection of, for example, BSC-1 cells with Tgp such as, for example, VVTgpI, and immunoprecipitation of cell lysates with a panel of MAbs prepared against VZV gpI, gpII, gpIII, gpIV and a VZV seropositive human serum or other conventional means known to those skilled in the art.

With respect to the fact that said Tgp is secreted from the infected cells, cells can be infected with Tgp such as, for example, VVTgpI, and radioactively labeled.

Antibodies against Tgp such as, for example, VVTgpI, can be generated in, for example, rabbit (e.g., RAnti-VVTgpI as described in the Examples). These antibodies can be tested to determine whether Tgp such as, for example, VVTgpI, is capable of inducing antibody response which is recognized by VZV gp. Mammalian cells such as, for example, BSC-1 cells can be infected with VZV and radioactively labeled in the absence or presence of tunicamycin (Vafai, et al., 1989). The Tgp of the present invention is capable of inducing antibody response which is recognized by native epitope (such as e1 as found in TgpI defined by Seq. Id. No. 1) and is capable of neutralizing VZV infectivity in the presence of complement.

Vaccines of the present invention may be administered parenterally (e.g., by intramuscular, subcutaneous, or intravenous injection). The amount required will vary with the antigenicity of the gene product and need only be an amount sufficient to induce an immune response typical of existing vaccines. Routine experimentation will easily establish the required amount. Typical initial dosages of vaccine could be about 0.001–100 mg antigen/kg body weight, with increasing amounts or multiple dosages used as needed to provide the desired level of protection.

The pharmaceutical carrier in which the vaccine is suspended or dissolved may be any solvent or solid that is non-toxic to the inoculated animal and compatible with the carrier organism or antigen gene product. Suitable pharmaceutical carriers include liquid carriers, such as normal saline and other non-toxic salts at or near physiological concentrations, and solid carriers, such as talc or sucrose. Adjuvants, such as Freund's adjuvant, complete or incomplete, may be added to enhance the antigenicity via the bronchial tubes, the vaccine is suitably present in the form of an aerosol. Booster immunizations may be repeated numerous times with beneficial results.

The present invention is also directed to a method for stimulating an immune response to chickenpox and shingles in a mammalian host. This method consists of administering an effective amount of secretory VZV Tgp (e.g., TgpI, TgpII, TgpIII, TgpIV or TgpV) under conditions sufficient to cause the production of antibodies to said Tgp, which are well recognized by one of ordinary skill in the art. The dosage effective amount is 0.001–100 mg of secretory VZV Tgp/kg body weight.

The subject invention also encompasses antibodies, either monoclonal or polyclonal, which are useful in the therapeutic control of chickenpox and/or shingles. Said antibodies can be prepared as described above and by injecting mammalian species, e.g., human, horse, rabbit, sheep, mice, etc. with inactivated Tgp or derivatives thereof and then purifying said antibodies employing the detection systems contemplated and described in further detail below.

In another embodiment, the present invention relates to the development of specific human or other (e.g., African green monkey kidney cells, COS monkey cells, HeLa cells or Chinese hamster cells) polyclonal or monoclonal antibodies raised against secretory VZV Tgp (I, II, III, IV or V), as well as human-mouse chimeric polyclonal or monoclonal antibodies for administration in passive immunization against chickenpox and/or shingles. Immunization refers to the process of inducing a continuing high antibody level in an organism i.e., in humans, which is directed against an antigen to which the organism has been previously exposed.

Passive immunization, as defined herein, refers to resistance (e.g., temporary or sustained protection against infection) based on giving preformed antibodies to a patient from an in vivo or in vitro source. The main advantage of passive immunization is the prompt availability of large amounts of antibodies against VZV as described in the above embodiment of the present invention.

A chimeric antibody, as defined herein, is an antibody molecule made by recombinant DNA technology involving immunoglobulin genes of two different species. The human-mouse chimeric antibody is produced by combining the Fab portion of the mouse immunoglobulin gene and the Fc portion of the human immunoglobulin gene by recombinant DNA techniques. The production of human-mouse chimeric antibodies is advantageous since large amounts of antibodies can be produced by this system and human-mouse chimeric antibodies can be recognized by cells of the human immune system whereas non-chimeric antibodies would not be recognized as easily by cells (e.g., phagocytic) of the human immune system. The chimeric antibodies can be produced in large amounts in the mouse system and can recognize VZV as contemplated in the present invention. Human-mouse immunoglobulins have also been found to make large amounts of antibodies in yeast and this system is also contemplated herein. The following references discuss the methodologies for producing such antibodies and are incorporated herein by reference: Morrison, et al., *P.N.A.S.*, 81:6851 (1984); Horowitz, et al., *P.N.A.S.*, 85:8678 (1988); and Tao, et al., *J. Immunol.*, 143:2595 (1989).

The present invention further contemplates the use of the above-described antibodies in a detection assay (immunoassay) for VZV.

A wide range of immunoassay techniques are available for utilization in the present invention as shown by reference to U.S. Pat. Nos. 4,016,043; 4,424,279; 4,018,653 and by Harlow, et al., supra. This, of course, includes both single-site and two-site, or "sandwich", assays of the non-competitive types, as well as in traditional competitive binding assays. Sandwich assays are among the most useful and commonly used assays and are favored for use in the present invention. A number of variations of the sandwich assay technique exist, and all are intended to be encompassed by the present invention.

In a typical forward assay, an unlabeled antibody is immobilized in a solid substrate and the sample to be tested brought into contact with the bound molecule. After a suitable period of incubation, for a period of time sufficient to allow formation of an antibody-antigen binary complex, a second antibody, labeled with a reported molecule capable of producing a detectable signal is then added and incubated, allowing time sufficient for the formation of a ternary complex of antibody-labeled antibody. Any unreacted material is washed away, and the presence of the antigen is determined by observation of the visible signal produced by the reported molecule. The results may either be qualitative, by simple observation of the visible signal, or may be 
quantitated by comparing with a control sample containing known amounts of hapten.

Variations on the forward assay include a simultaneous assay, in which both sample and labeled antibody are added simultaneously to the bound antibody, or a reverse assay in which the labeled antibody and sample to be tested are first combined, incubated and then added to the unlabeled surface bound antibody. These techniques are well known to those skilled in the art, and the possibility of minor variations will be readily apparent to those skilled in the art.

As used herein, "sandwich assay" is intended to encompass all variations on the basic two-site technique. For example, these antibodies may be used to detect secretory Tgp, e.g., TgpI, TgpII, TgpIII, TgpIV, TgpV or more specifically, secretory gpI as defined by Seq. Id. No. 1, by use of specific antigenic determinants (e.g., e1 epitope) as immobilized immunoadsorbants. Serum is obtained from subjects to be tested and said serum contacted to the immobilized viral immunoadsorbants. If said serum contains antibodies to said immunoadsorbants, an antibody-adsorbant conjugate will result. After removing excess serum and non-bound antibodies, a second antibody specific to a first antibody, said first antibody being capable of forming a conjugate with said immunoadsorbant, is added thus resulting in a double antibody-adsorbant conjugate. This double antibody-adsorbant conjugate will only result if the test serum contains antibodies to the immunoadsorbant. Consequently, standard detection techniques can be used to identify the conjugate.

In another immunoassay, the competitive binding assay, a limiting amount of antibody specific for the molecule of interest (either an antigen or hapten) is combined with specific volumes of solutions containing an unknown amount of the molecule to be detected and a solution containing a detectably labeled known amount of the molecule to be detected or an analog thereof. Labeled and unlabeled molecules then compete for the available binding sites on the antibody. Phase separation of the free and antibody-bound molecules allows measurement of the amount of label present in each phase, thus indicating the amount of antigen or hapten in the sample being tested. A number of variations in this general competitive binding assay currently exist.

In any of the known immunoassays, for practical purposes, one of the antibodies to the antigen (secretory truncated VZV gp) will be typically bound to a solid phase and a second molecule, either the second antibody in a sandwich assay, or, in a competitive assay, the known amount of antigen, will bear a detectable label or reporter molecule in order to allow visual detection of an antibody-antigen reaction. When two antibodies are employed, as in the sandwich assay, it is only necessary that one of the antibodies be specific for, e.g., secretory truncated VZV gpI, II, III, IV or V. The following description will relate to a discussion of a typical forward sandwich assay; however, the general techniques are to be understood as being applicable to any of the contemplated immunoassays.

In the typical forward sandwich assay, a first antibody having specificity for, e.g., secretory TgpI, II, III, IV or V or the mature polypeptide as defined by Seq. Id. No. 1 or its antigenic fragments is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs or microplates, or any other surface suitable for conducting an immunoassay. The binding processes are well-known in the art and generally consist of cross-linking, covalently binding, or physically adsorbing the molecule to the insoluble carrier. Following binding, the polymer-antibody complex is washed in preparation for the test sample. An aliquot of the sample to be tested is then added to the solid phase complex and incubated at 25° C. for a period of time sufficient to allow binding of any subunit present in the antibody. The incubation period will vary, but will generally be in the range of about 2–40 minutes. Following the incubation period, the antibody subunit solid phase is washed and dried and incubated with a second antibody specific for a portion of the hapten. The second antibody is linked to a reporter molecule which is used to indicate the binding of the second antibody to the hapten.

By "reporter molecule", as used in the present specification and claims, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionucleotide-containing molecules.

In the case of an enzyme immunoassay (EIA), an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphates, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; and for peroxidase conjugates, 1,2-phenylenediamine, 5-aminosalicyclic acid, or tolidine are commonly used. It is also possible to employ fluorogenic substrates, which yield a fluorescent product rather than the chromogenic substrates noted above.

The enzyme-labeled antibody is added to the first antibody hapten complex, allowed to bind, and then excess reagent is washed away. A solution containing the appropriate substrate is then added to the ternary complex of antibody-antigen-antibody. The substrate will react with the enzyme linked to the second antibody, giving a qualitative visual signal, which may be further quantitated, usually spectrophotometrically, to give an indication of the amount of hapten which was present in the sample.

Alternately, fluorescent compounds, such as fluorescein and rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic color visually detectable with a light microscope. As in the EIA, the fluorescent labeled antibody is allowed to bind to the first antibody-hapten complex. After washing off the unbound reagent, the remaining ternary complex is then exposed to the light of the appropriate wavelength, the fluorescence observed indicates the presence of the hapten of interest. Immunofluorescence and EIA techniques are both very well established in the art and are particularly preferred for the present method. However, other reporter molecules, such as radioisotope, chemiluminescent of bioluminescent molecules, may also be employed. It will be readily apparent to the skilled technician how to vary the procedure to suit the required purposes.

It will also be apparent that the foregoing can be used to detect directly or indirectly (i.e., via antibodies) VZV.

The present invention also contemplates a method of diagnosing VZV comprising contacting serum, tissue or tissue extracts of an individual to be tested with an antibody against secretory truncated VZV gp (such as, for example, gpI, gpII, gpIII, gpIV or gpV) or an active fragment thereof, for a time and under conditions necessary to form an antibody-antigen complex, and then detecting any resultant antibody-antigen complex. Such conditions would be well recognized by an artisan of ordinary skill in the art.

In a further embodiment, the present invention also relates to a kit for the detection of antibodies produced in response to secretory Tgp (such as, for example, TgpI, TgpII, TgpIII, TgpIV, TgpV, TgpIBglII as defined by Seq. Id. No. 1 or TgpIXmaIII as defined by Seq. Id. No. 2) and its antigenic fragments (epitope(s)), the kit being compartmentalized to receive a first container adapted to contain an antibody having specificity for said antibody to Tgp or fragments thereof and a second container containing an antibody specific for first antibody and being labeled with a reporter molecule capable of giving a detectable signal. If the reporter molecule is an enzyme, then a third container, containing a substrate for said enzyme is provided.

The diagnostic kit of the present invention can be used to detect the antibody status of VZV glycoproteins. This kit represents a rapid method of diagnosis and detection of VZV in individuals exhibiting various clinical manifestations of VZV as well as in vaccinated individuals.

EXAMPLES

1) Materials And Methods

Varicella-zoster virus (VZV) strain VZV86, originally isolated from a patient with zoster, was grown and propagated in African green monkey kidney cells (BSC-1) by the cocultivation method described in Vafai et al., *Virus Res.* 13:319–336 (1989). Vaccinia virus (strain IHDJ) was grown in BSC-1 cells at a multiplicity of infection (m.o.i.) of 0.01 plaque forming units (PFU) as described in Cabirac, et al., *Virus Res.* 10:205–214 (1988).

2) Preparation of Monoclonal and Polyclonal Antibodies

Monoclonal antibodies (MAbs) against VZV glycoprotein I (gpI) and gpIV (MAb79.7, MAbC1, MAbG7, MAbG6); gpII (MAbF8) and gpIII (MAbE10) were prepared by procedures described previously in Vafai, et al., *J. Virol.*, 52:953–959 (1984); Vafai, et al., *J. Virol.* 62:2544–2551 (1988); Cabirac, et al., *Virus Res.* 10:205–214 (1988); and Vafai, et al., Virus Res. 13:319–336 (1989). Human sera were obtained from a Zoster patient six weeks after the onset of skin rash. Antibodies against VZV virions were prepared in rabbit as described in Vafai et al., *Virus Res.* 7:325–333 (1987).

3) Construction of Recombinant Vaccinia Virus

FIG. 1 illustrates the construction of the insertion vector used to generate a recombinant vaccinia virus carrying a truncated VZV gpI (VVTgpIBglII). The recombinant plasmid (pGEM-4) containing VZV gpI gene (Vafai, et al., *J. Virol.* 62:2544–2551 (1988)) was cleaved with BglII downstream from e1 epitope at VZV nucleotide sequence 116287 (Davison and Scott, *J. Gen. Virol.* 67:1759–1816 (1986)) and with EcoRI in the pGEM-4 polylinker. The truncated gpI gene, encoding a polypeptide of 159 amino acids, was electroeluted, blunt-ended with T4 DNA polymerase as described (Maniatis, et al., *Molecular Cloning: A Laboratory Manual*, Cold Spring Harbor Laboratory, Cold Spring Harbor, New York (1982)), and ligated into the SmaI site of the insertion vector pSC11 (Chakrabarti, et al., *Mol. Cell. Biol*, 5:3403–3409 (1985)). The recombinant plasmid was designated pVVTgpIBglII (and is shown in FIG. 1). The recombinant vaccinia virus was generated by the method described by Mackett, et al. "The Construction and Characterization of Vaccinia Virus Recombinants Expressing Foreign Genes" in *DNA Cloning: A Practical Approach*, (D. M. Glover, ed.), IRL Press, Oxford, p. 191–211 (1985) with modifications. 143B TK⁻ cells (Mackett, et al., 1985) were grown overnight in the absence of bromodeoxyuridine (BudR), and were then infected with vaccinia virus (strain IHDJ) at a m.o.i. of 0.01 PFU and incubated at 37° C. for 90 min. Infected cells were then transfected with 30 μg of pVVTgpI and 50 μg of Lipofectin reagent (BRL) according to the manufacturer's instructions. Cells were harvested 48 hours post-infection-transfection and the resulting virus stock was passaged twice in TK⁻ cells in the presence of 25 μg/ml BudR. Recombinant vaccinia virus was distinguished from spontaneous TK⁻ virus by straining with bluo-gal (BRL) and was clonally isolated by three cycles of plaque purification.

In order to prepare a more immunogenic secretory truncated VZV gpI, the same methodology was employed with the modification that the recombinant plasmid (pGEM-4) containing the VZV gpI gene was cleaved with XmaIII at VZV nucleotide sequence 117342 and with EcoR1 (instead of BglII and Eco R1). The truncated gpI gene, encoding the N-terminal region of gpI with 511 amino acid residues, was electroeluted, blunt-ended and ligated into pSCII as described above. The recombinant plasmid was designated pVVTgpIXmaIII. The recombinant vaccinia virus was generated as described above and designated VVTgpIXmaIII.

4) Expression of Recombinant Vaccinia Virus

The expression of recombinant vaccinia virus carrying the truncated VZV gpI gene (designated VVTgpIBglII and VVTgpIXmaIII) were analyzed by infection of BSC-1 cells with VVTgpI at a m.o.i. of 1.0 PFU. After 22-hour incubation at 37° C., infected cells were starved for methionine in methionine-free medium for 1 hour and were then labeled with [35S] methionine (100–200 uci/ml) for 1 hour. Cells were then washed three times with cold phosphate-buffered saline and disrupted in 4 ml of lysis buffer (0.02 M sodium phosphate, pH 7.6, 0.1 M NaCl, 1% Triton x-100, 0.5% deoxycholate, 0.1% SDS). Lysates were kept on ice for 2 hours and centrifuged at 40,000 rpm in a Beckman SW60 rotor for 2 hours at 5° C. Supernatants were stored at −70° C. until immunoprecipitation with monoclonal and polyclonal antibodies prepared against VZV proteins. (See FIGS. 2 and 3.)

Figure 2:
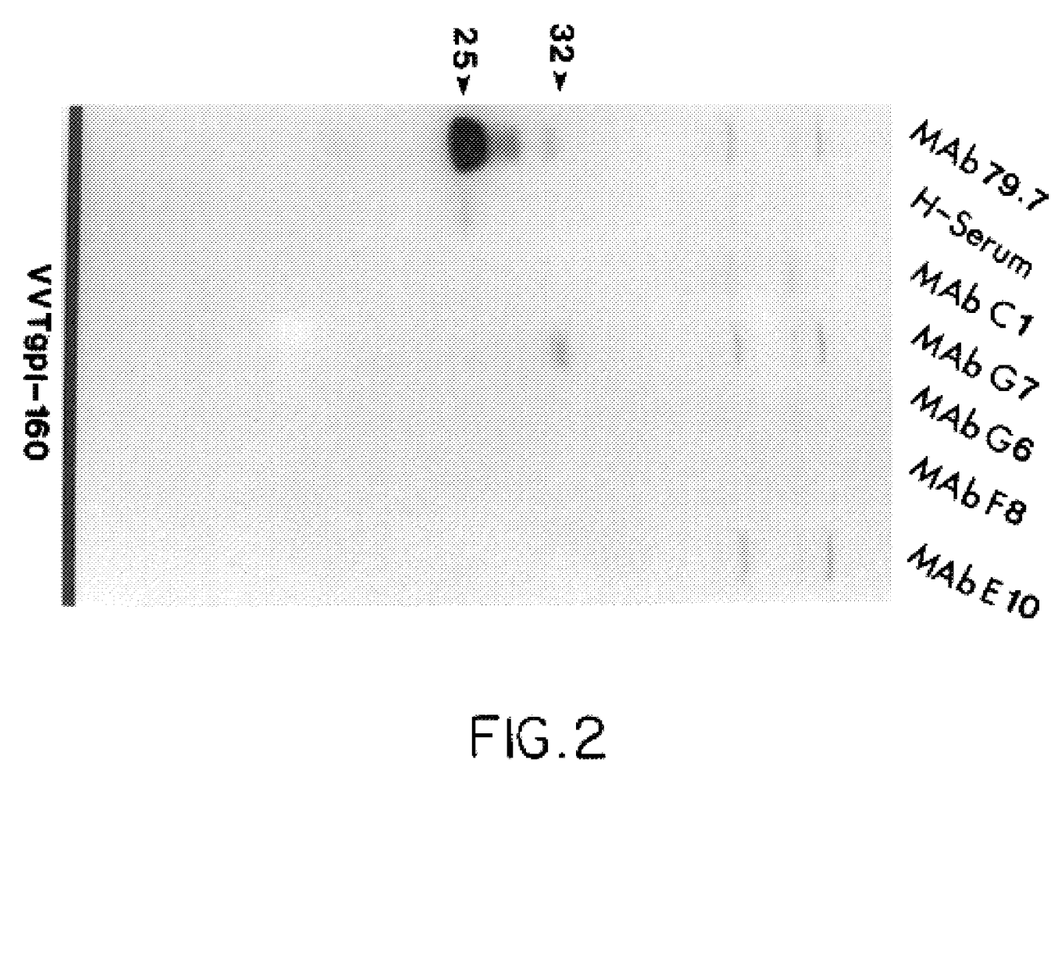

The results shown in FIG. 2 demonstrate the expression of a primary translation product of 25 kDa by VVTgpIBglII which was processed to a 32 kDa polypeptide during 1 hour labeling period. Both 25 kDa and 32 kDa proteins can be recognized by MAb79.7 which is directed against e1 epitope (Vafai, et al., 1988). Human serum reacts with the 25 kDa species (FIG. 2, line 2) and longer exposures of the gels indicate a faint reactivity of human serum with mature form (32 kDa) of TgpI. The 32 kDa protein was also reacted with MAbG7 (FIG. 2, line 4) which recognizes the fully glycosylated form of VZV gpI. However, MAbC1, which is directed against VZV gpI but only recognizes epitope(s) other than e1, does not react with TgpI (FIG. 2, line 3). MAbs directed against VZV gpIV (MAbG6), gpII (MAbF8) and gpIII (MAbE10) do not also react with the precursor-product of TgpI (FIG. 2, lines 5, 6, 7), indicating the specificity of TgpI for MAb79.7.

These results indicate that the TgpI expressed by VVTgpIBglII retains the native conformation necessary for recognition by MAb79.7 as well as VZV seropositive human serum. The primary translation product of TgpI of 25 kDa has been found to be larger than the expected 17.5 kDa deduced from 159 amino acid residues encoded by the TgpI.

Figure 3:
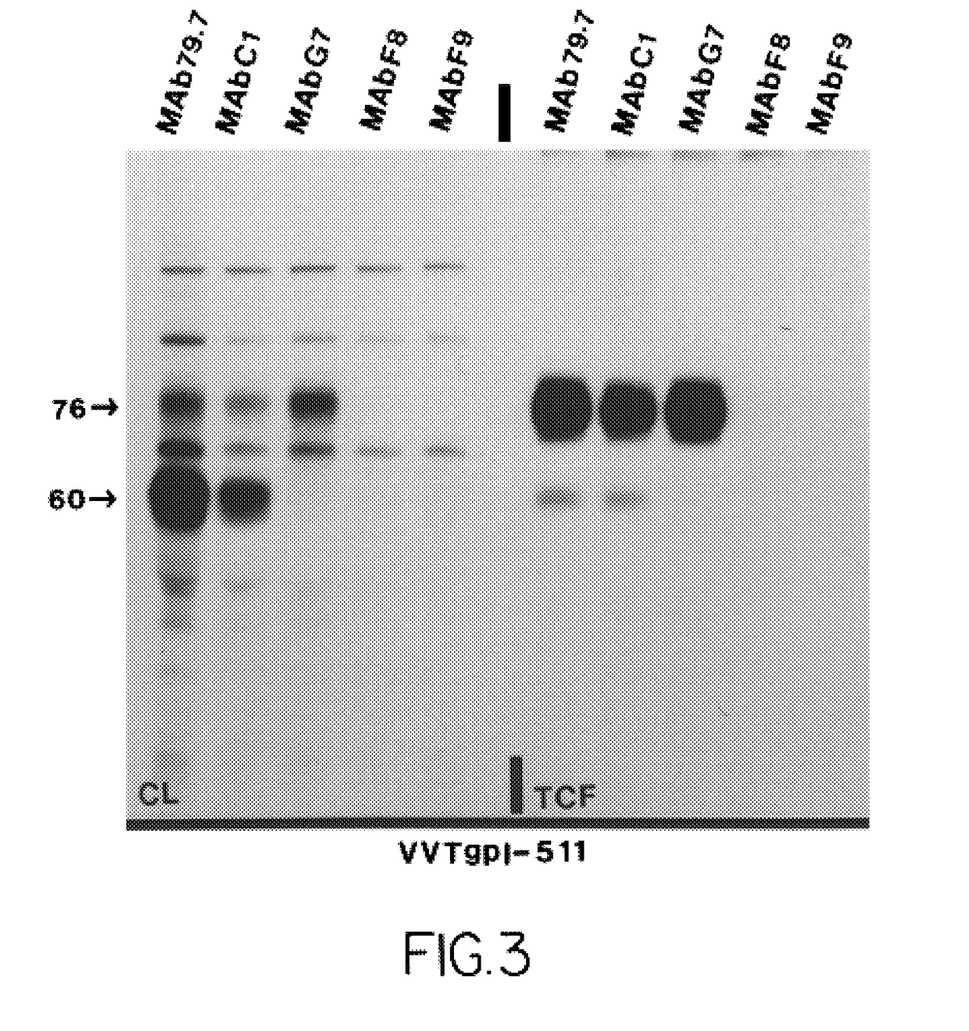

The results shown in FIG. 3 demonstrate the expression of a primary translation product of 60 kDa by VVTgpIXmaIII which was processed to a 76 kDa polypeptide during one hour labeling period. Both 60 kDa and 76 kDa proteins are recognized by MAb79.7 and MAbC1, which recognize the precursor-product of VZVgpI, and MAbG7, which recognizes only the mature and fully glycosylated forms of VZVgpI (FIG. 3, lanes 1, 2 and 3). MAbF8 (directed against gpII) and MAbF9 (directed against VZV NCP) did not react with the precursor-product of TgpI-XmaIII (FIG. 3, lanes 4 and 5). The reactivity of MAbC1 with TgpIXmaIII but not with TgpIBglII evidences the presence of additional epitope (s) on TgpIXmaIII.

5) Analysis of Secreted VZV Truncated gpI

BSC-1 cells were infected with VVTgpIBglII at a m.o.i. of 1.0 PFU and after 22-hour incubation period, cells were pulse-labeled with [35S] methionine (300 μci/ml) for 10 min. Cells were either harvested or washed five times with serum-free medium and the label was chased for 1, 2, 3 and 7 hours. Uninfected cells were pulse-labeled for 10 min. and chased for 7 hours. Cell lysates were prepared as described above and immunoprecipitated with MAb79.7 which is directed against VZV gpIBglII epitope (e1) (Vafai, et al., *J. Virol.* 62:2544–1551 (1988)) and MAbC1 which is directed against VZV gpIBglII but recognizes epitope(s) other than e1. Tissue culture fluids from uninfected and VVTgpIBglII-infected cells were collected and centrifuged for 10 min. in a microfuge. Supernatants were collected and after addition of equal volume of lysis buffer to each sample, the samples were centrifuged at 40,000 rpm in a Beckman SW60 rotor for 2 hours at 5° C. Supernatants were immunoprecipitated with MAb79.7 and MAbC1. (See FIG. 4.)

Figure 4A:
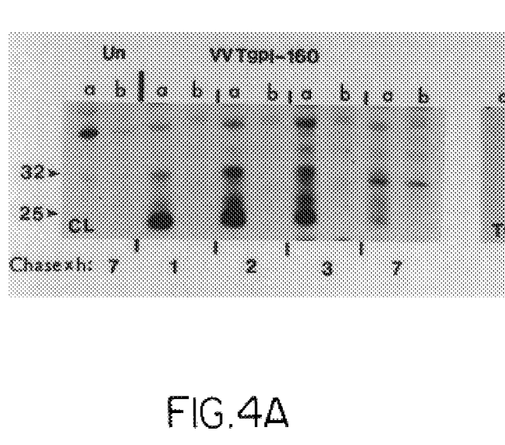
Figure 4B:
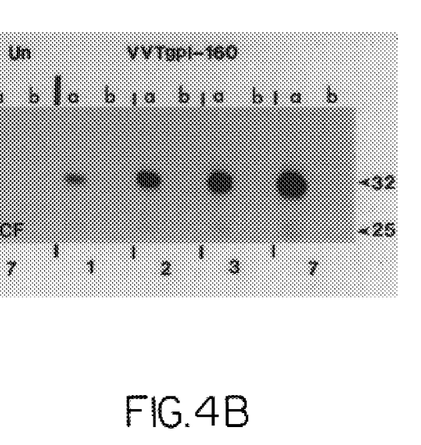

The results shown in FIG. 4 demonstrate that precursor TgpIBglII (25 kDa) detected in the infected cells during a 10-min. pulse-labeling period is processed to a 32 kDa protein species during 1 hour chase-period and that the intensity of both 25 kDa and 32 kDa bands decrease during 7 hours chase-period (FIG. 4, CL). The results also show that the mature glycosylated form of TgpIBglII (32 kDa) appeared in tissue culture fluid of the infected cells within 1 hour chase-period and the intensity of the 32 kDa TgpIBglII increases during a 7-hour chase-period (FIG. 4, TCF). These results indicate that the fully processed form of TgpIBglII is released from the infected cells and is recognized by MAb79.7 but not MAbC1 which is directed only against gpI epitope(s) other than e1. In addition, western-blot analysis of the 32 kDa TgpIBglII purified from the infected tissue culture fluids shows that secretory TgpIBglII was recognized by MAb79.7.

Figure 5:
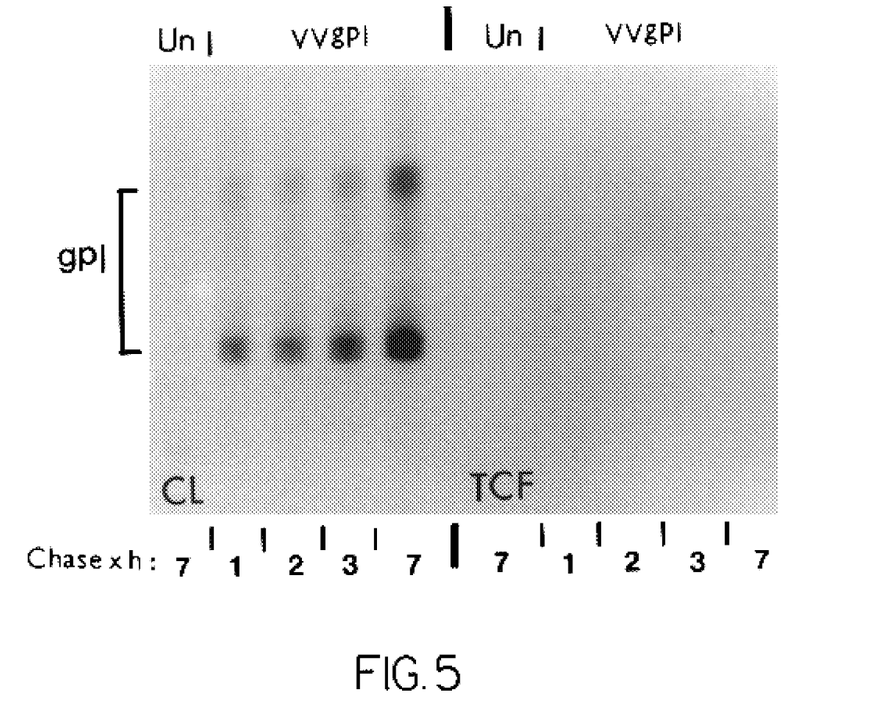

Controls for these experiments were provided by infection of BSC-1 cells with a recombinant vaccinia virus carrying the untruncated (full-size) VZV gpI gene and expressing untruncated VZV gpI (VVgpI) (Cabirac, et al., *Virus Res.* 10:205–214 (1988)). Pulse-chase experiments as above were performed. In contrast to VVTgpIBglII, analysis of cell lysates and tissue culture fluid from VVgpI-infected cells indicated that native VZV gpI was not secreted from the infected cells (FIG. 5).

To determine whether TgpI-XmaIII is secreted from the cells, infected cells were pulse-labeled with [35S]methionine for 1 hour, washed with serum-free medium and incubated with serum-free media for 2 hours. Tissue culture fluids (TCF) were harvested and immunoprecipitated with MAbs as described above. The results demonstrate that the mature and fully glycosylated form of TgpIXmaIII was secreted from the cells and was recognized by anti-gpI MAbs (FIG. 3, Lanes 7, 8 and 9) but not by MAbF8 and MAbF9, which are directed against VZVgpII and VZV NCP, respectively (FIG. 1, lanes 10 and 11).

6) Preparation of Anti-VVTgpI Antibodies

Antibodies to VVTgpI were generated in a rabbit by immunization procedures described previously (Vafai, et al., *Virus Res.* 7:325–333 (1987) and *Virus Res.* 13:319–336 (1989)). A New Zealand white female rabbit was immunized subcutaneously at multiple sites in the back and hind legs. After a preimmunization bleed (for control sera) the animal received $1 \times 10^7$ PFU/ml of VVTgpI. This was followed by three weekly injections, each consisting of $1 \times 10^7$ PFU/ml of VVTgpI. The animal was bled seven days after the last injection and the serum (designated RAnti-VVTgpI) was assayed by immunoprecipitation as described below.

7) Radioactive Labeling of VZV-Infected Cell Proteins

VZV was grown in BSC-1 cells by cocultivation and after 48 hours, infected cells were labeled with [35S] methionine (300 pci/ml) for 10 min. in the absence or presence of tunicamycin (15 μg/ml). Cells were either harvested or washed three times with serum-free medium, and the label was chased in normal medium for 2 hours in the absence or presence of tunicamycin (15 μg/ml). Cells were then washed three times with cold phosphate-buffered saline and cell lysates were prepared as described above and immunoprecipitated with RAnti-VVTgpI.

8) Immunoprecipitation

Cell lysates (400 μl) from uninfected, VVTgpIBglII-infected, VVgpI-infected, VZV-infected cells and lysates (500 μl) tissue culture fluid from uninfected, VVTgpI-infected and VVgpI-infected cells were incubated for 2 hours at 4° C. with 40 μl of a 10% Formalin-fixed suspension of protein A-containing *Staphylococcus aureus* Cowan I (Kesler, *J. Immunol.* 115:1614–1617, 1975). After centrifugation at 9,000×g for 20 min., VZV-specific proteins were immunoprecipitated at 4° C. for 20 hours in the presence of 50 μl of polyclonal antibodies (human sera and RAnti-VVTgpI) or 100 μl of monoclonal antibodies prepared against VZV proteins. Finally, 30 μl of a 10% Formalin-fixed *S. aureus* suspension was added, and after 2 hours at 4° C., absorbed immune complexes were washed three times with lysis buffer and suspended in 20 μl of TNE buffer (50 mM Tris, pH 7.4, 150 mM NaCl, 5 mM EDTA). After addition of 10 μl of 3×sample buffer (150 mM Tris, pH 7.0, 6% SDS, 15% 2-mercaptoethanol, 0.03% bromophenol blue), the suspension was heated in boiling water for 4 min., cooled on ice, and analyzed by 8 to 12% polyacrylamide SDS-PAGE as described in Vafai, et al., *J. Virol.* 52:953–959, 1984 and *J. Virol.* 62:2544–2551, 1988. (See FIG. 5.)

Figure 6A:
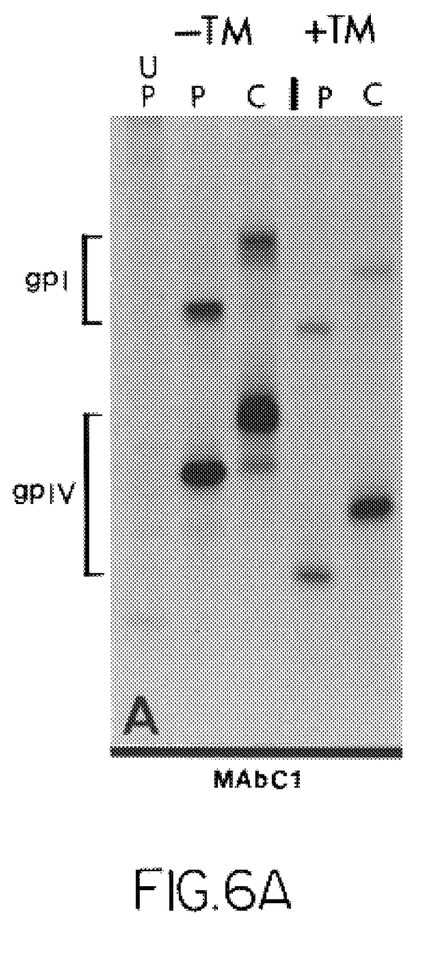
FIG. 6 demonstrates immunoprecipitation of VZV-infected cells with rabbit antibodies prepared against recombinant vaccinia virus carrying a truncated VZV gpI and containing e1 epitope (VVTgpI). Cells were infected with VZV and after 48 hours, cells were pulse-labeled with [35S]
Figure 6B:
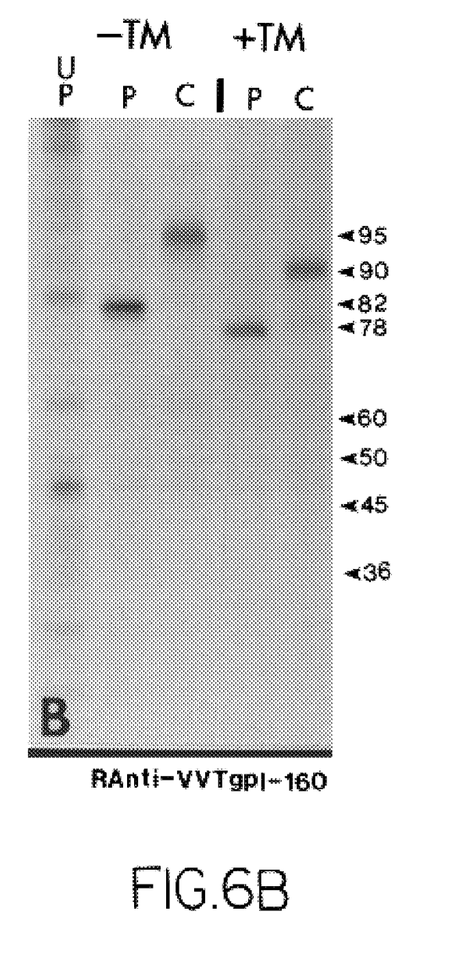

Cell lysates were immunoprecipitated with MAbC1 which recognizes VZV gpI and gpIV and RAnti-VVTgpIBglII and analyzed by SDS-PAGE. As demonstrated in FIGS. 6A and B, the results show that similar to MAbC1, RAnti-VVTgpIBglII reacts with precursor-products of native VZV gpI in the presence or absence of tunicamycin. This shows that e1 epitope expressed by VVTgpIBglII induced antibody response which is recognized by VZV native gpI e1 epitope.

9) Neutralization Tests

Neutralization tests were performed by the constant virus-varying serum technique as described (Vafai, et al., 1987). Briefly, BSC-1 cells ($10^8$) were infected with VZV by cocultivation. After three days, when infected cultures showed 80–90% cytopathic effects, cells were scraped into the tissue culture medium, centrifuged at 2,000×g for 20 min. at 4° C. and the cell pellet was resuspended in 4 ml of serum-free medium. The cell suspension was dounce-homogenized (150 strokes) on ice in a Teflon-coated homogenizer. The homogenates were centrifuged at 800×g for 10 min. and the supernatants were used for neutralization tests. Aliquots (0.5 ml) containing 100–200 PFU were mixed with equal volumes of different dilutions (0,1:10, 1:50 and 1:100) of RAnti-VVTgpI or rabbit anti-VZV antibodies (RAnti-VZV) prepared against VZV virions (Vafai, et al., 1987) or preimmune sera and 0.25 ml guinea pig complement. The mixture were incubated at 37° C. for 2 hours and inoculated into 2 wells of BSC-1 cells grown in 6-well plates. After incubation at 37° C. for 3 hours, the inoculum was removed, the cells were washed and overlaid with medium containing 2% fetal bovine serum (FBS) and incubated at 37° C. for 5–7 days. Cells were then fixed with formaldehyde, stained with cresyl violet and plaques were counted as described (Vafai, et al., 1984).

The results show a plaque reduction of, for example, 100% with 1:10 dilution of RAnti-VZV antibodies prepared against purified VZ virions (Vafai, et al., 1987) in the presence or absence of complement and a plaque reduction of 50% with 1:10 dilution of RAnti-VVTgpI in the presence of complement.

We claim:

1. A recombinant DNA expression vector comprising a nucleotide sequence which expresses, in an infected, transfected or transformed host, a Varicella-zoster virus (VZV) truncated glycoprotein I (gpI) which is secreted extracellularly from said host and wherein said glycoprotein causes a VZV antibody response in mammals.

2. The recombinant DNA expression vector of claim 1 wherein said infected, transfected or transformed host cell is selected from the group consisting of green monkey kidney cells (BSC-1), COS monkey cells, HeLa cells, hamster kidney cells, human fibroblast cells, and human tissue cells.

3. The recombinant DNA expression vector according to claim 1 or 2 wherein said nucleotide sequence expresses in an infected, transfected or transformed host a mature polypeptide encoded by SEQ ID NO:1 or SEQ ID NO:2.

4. A plasmid encoding a Varicella-zoster virus glycoprotein which is secreted extracellularly and which causes an antibody response in mammals.

5. A process for producing a secretory truncated Varicella-zoster virus glycoprotein, said process comprising the steps of:
   a) providing a vector comprising a nucleotide sequence coding for said glycoprotein, wherein the nucleotide sequence is selected from the group of nucleic acids which encode a continuous nucleotide sequence of a Varicella-zoster virus glycoprotein having at least about 336 nucleotides from the C-terminal region of the glycoprotein deleted such that said glycoprotein is secreted extracellularly from said host and wherein said glycoprotein elicits a VZV antibody response in mammals;
   b) incorporating the vector into the host; and
   c) maintaining the host containing the vector under conditions suitable for expression of the nucleotide sequence into said glycoprotein.

6. The process of claim 5 wherein said vector includes a promoter operationally associated with said nucleotide sequence.

7. The process of claim 5 or 6 wherein said host is a mammalian cell and wherein said nucleotide sequence further includes a region of nucleotides which encodes a leader sequence.

8. The process of claim 7 wherein said mammalian cells are selected from the group consisting of green monkey kidney cells (BSC-1), COS monkey cells, HeLa cells, hamster kidney cells, human fibroblast cells and human tissue cells.

9. The process according to claim 8 wherein said glycoprotein is a polypeptide of the open reading frame defined by the 159 amino acid sequence of SEQ ID NO:1 or the 511 amino acid sequence of SEQ ID NO:2.

10. The process of any one of claim 8 or 9 wherein said expression vector is a plasmid.

11. A recombinant vaccinia virus vector comprising a nucleotide sequence which expresses, in an infected, transfected or transformed green monkey kidney cell (BSC-1), a Varicella-zoster virus (VZV) truncated glycoprotein I (gpI) which is secreted extracellularly from said BSC-1 cell and wherein said glycoprotein causes a VZV antibody response in mammals.

12. The recombinant vaccinia expression vector according to claim 11 wherein said nucleotide sequence expresses, in an infected, transfected or transformed BSC-1 cell, a mature polypeptide encoded by SEQ ID NO:1 or SEQ ID NO:2.

13. A process for producing a secretory truncated Varicella virus glycoprotein I, said process comprising the steps of:
   a) providing a vaccinia virus vector comprising a nucleotide sequence coding for said glycoprotein, wherein said nucleotide sequence is expressed by a green monkey kidney cell (BSC-1) comprising said vaccinia vector, and wherein said nucleotide sequence is selected from the group of nucleic acids which encode a continuous nucleotide sequence of a Varicella-zoster virus glycoprotein having at least about 336 nucleotides from the C-terminal region of the glycoprotein deleted such that said glycoprotein is secreted extracellularly from said BSC-1 cell and wherein said glycoprotein elicits a VZV antibody response in mammals;
   b) incorporating said vaccinia vector into said BSC-1 cell; and
   c) maintaining said BSC-1 cell containing the vaccinia vector under conditions suitable for expression of said nucleotide sequence into said glycoprotein.

14. The process of claim 13 wherein said vaccinia vector includes a promoter operationally associated with said nucleotide sequence.

15. A process according to claim 13 wherein said glycoprotein is a polypeptide of the open reading frame encoded by SEQ ID NO: 1 or SEQ ID NO:2.

* * * * *